United States Patent [19]

Preuss

[11] 4,430,270
[45] Feb. 7, 1984

[54] PROCESS FOR THE PRODUCTION OF DELTA 4-C21-STEROID COMPOUNDS

[75] Inventor: Wolfgang Preuss, Monheim, Fed. Rep. of Germany

[73] Assignee: Henkel Kommanditgesellschaft auf Aktien, Dusseldorf-Holthausen, Fed. Rep. of Germany

[21] Appl. No.: 407,791

[22] Filed: Aug. 13, 1982

Related U.S. Application Data

[63] Continuation-in-part of Ser. No. 262,967, May 12, 1981, abandoned.

[30] Foreign Application Priority Data

May 12, 1980 [AT] Austria .................................. 2536/80
May 16, 1980 [AT] Austria .................................. 2630/80

[51] Int. Cl.³ .............................................. C07J 1/00
[52] U.S. Cl. ............................. 260/397.1; 260/397.3; 260/397.45
[58] Field of Search ................... 260/397.3, 397, 397.1, 260/397.45

[56] References Cited

U.S. PATENT DOCUMENTS 4,252,730  2/1981  Krbechek .......................... 260/397.3
4,252,731  2/1981  Krbechek .......................... 260/397.3
4,252,732  2/1981  Krbechek .......................... 260/397.3

*Primary Examiner*—Elbert L. Roberts
*Attorney, Agent, or Firm*—Hammond & Littell, Weissenberger and Muserlian

[57] ABSTRACT

C21-steroid compounds with a nitrogen function in the 20-position corresponding to general formula I below

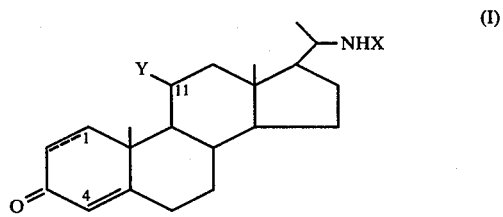

in which Y is hydrogen, a hydroxyl group or, together with the C-atom substituted by Y, represents a carbonyl group or may even be replaced by a 9(11)-ene bond and in which X is hydrogen, acyl, a carbonic acid ester residue or, together with the adjacent hydrogen atom on the nitrogen, represents a carbonyl group, may be obtained by converting the steroid-C20-carboxylic acid halides structurally analogous to the required reaction product into the corresponding carboxylic acid azide and either transforming the carboxylic acid azide thus formed into the C20-isocyanate through the elimination of nitrogen and, if desired, converting the C20-isocyanate thus obtained into the C20-carbamate and/or the C20-amine or directly transforming the carboxylic acid azide into the C20-amine. The compounds thus produced corresponding to general formula I, in which Y represents an oxygen function or in which the substituent Y is replaced by a 9(11)-ene bond, are new. The 20 amino compounds are readily converted to progesterone and other useful steroids.

21 Claims, No Drawings

4,430,270

PROCESS FOR THE PRODUCTION OF DELTA 4-C21-STEROID COMPOUNDS

This is a continuation-in-part of Ser. No. 262,967, filed May 12, 1981, now abandoned.

BACKGROUND OF THE INVENTION

European Patent Application No. 004913 as laid open describes inter alia a process for the production of 17-C-steroid-α-propionic acid compounds, particularly 3-oxo-pregna-4-ene-20-carboxylic acid (Δ4-BNC) and/or 3-oxo-pregna-1,4-diene-20-carboxylic acid (Δ1,4-BNC), by microbial side chain degradation on 17-C-side chain steroid substrates. By using defect mutant microorganisms grown and selected in a certain manner, which give steroid compounds containing the 17-C-α-propionic acid residue even in the absence of inhibitors which inhibit degradation of the steroid ring and/or growth inhibitors, it is possible to obtain Δ4-BNC and, in particular, Δ1,4-BNC in commercial quantitites. Another of this process is described in laid open European Patent Application No. 0015308.

German Offenlegungsschrift No. 28 39 033 also laid open, describes structurally analogous steroid-20-carboxylic acids containing an additional double bond in the 9(11)-position and a process for their production. In particular, one possibility of producing Δ1,4,9(11)-BNC is described therein. Δ4,9(11)-BNC is described in U.S. Pat. No. 4,062,880. All these compounds, particularly Δ4-BNC, Δ1,4-BNC and Δ1,4,9(11)-BNC, contain a functional group in only the 3-position of the ring system. However, all pharmacologically active corticosteroids contain additional oxygen functions. The 11,17 and 21 positions inter alia are particularly important in this respect. Normally, some of these oxygen functions are chemically introduced, including in particular the 17 and 21 positions.

By contrast, oxidation of the 11-position is steroid compounds is preferably carried out microbially. Several such microbial steroid oxidation processes are described in the literature. In this connection, reference is made to the following publications and to the original Articles quoted therein:

F. Drawert "Biosynthese von Hydroxy-Verbindungen (Biosynthesis of Hydroxy-Compounds)"; Houben-Weyl "Methoden der organischen Chemie" (1978) 6/1d, pages 378 to 388; T. H. Stoudt, Adv. Appl. Microbiol. 2 (1960), pages 190 to 195 and W. Charney and H. L. Herzog "Microbial Transformations of Steroids", Academic Press (1967) New York, N.Y. page 29.

The microbial 11-hydroxylation of a variety of steroid compounds and the synthesis products obtained are described in these publications with numerous reference to certain microorganism strains, particularly from the class of fungi.

The 11β-hydroxyl or 11-oxo configuration is generally required for strong, pharmacological activity. Steroids hydroxylated in the 11β-position are obtained either by using microorganism strains which introduce a hydroxyl group of the type in question stereoselectively or by using other microorganisms which hydroxylate in the 11β-position either predominantly or completely stereoselectively. In this case, the 11β-hydroxylated steroids are obtained by chemical oxidation to the 11-ketone in a first step, followed by reduction with a suitable reducing agent. The 11β-hydroxy compound can be formed stereoselectively. So far as the relevant literature on this subsequent chemical transformation is concerned, reference is made for example to I. F. Fieser, M. Fieser Steroide "(Steroids)", Verlag Chemie (Weinheim 1961), pages 737 et seq and to the original literature reference cited therein, J. Am. Chem. Soc. 77, 4436 (1955).

Pharmacologically important steroid compounds and intermediate products for their production, for example progesterone, compounds of the cortisone series and compounds of the prednisone series, no longer contain the C-22-carboxyl group which is present as a substituent in the 20-position in BNC-compounds.

Earlier and co-pending commonly assigned Patent Applications describe the transformation of the 20-carboxyl group in the BNC-compounds mentioned into the corresponding 20-acid halide group. In particular, the corresponding acid chlorides and their production are described. Thus, commonly-assigned earlier European Patent Application No. 81,100,145.2 describes inter alia pregna-1,4-diene-3-one-20-carbonyl chloride (Δ1,4-BNC-chloride) and a process for its production. This acid chloride, which is a functional derivative of the associated Δ1,4-BNC, is suitable for use as a starting material for subsequent reactions for the further structural transformation of the side chain substituent in the 17-position of the steroid ring skeleton. The production of other steroid-20-carboxylic acid halides of the type mentioned is described in commonly-assignly copending Patent Application Ser. No. 262,971, filed May 12, 1981, entitled "New Steroid-20-carboxylic acid compounds and a process for their production", now abandoned in favor of its continuation-in-part application Ser. No. 423,276, filed Sept. 24, 1982, Priority Austria A 2629/80 filed May 16, 1980 and 262,965, filed May 12, 1981, entitled "New pregnane-20-carboxylic acid derivatives and a process for their production", now abandoned in favor of its continuation-in-part application Ser. No. 407,790, filed Aug. 13, 1982, Priority Austria No. A 2535/80 filed May 12, 1980.

OBJECTS OF THE INVENTION

The object of the present invention is to transform monounsaturated or, in particular, polyunsaturated BNC-20-carboxylic acids, which may even contain an oxygen function in the 11-position, through degradation of the carboxyl group in the 20-position into C21-nitrogen compounds which in turn represent valuable steroid compounds and, in particular, valuable intermediate products for the production of steroid compounds of the progesterone type and derivatives thereof.

More particularly, the object of the invention is to transform Δ4-BNC, Δ1,4-BNC and their derivatives containing an oxygen function in the 11-position and Δ1,4,9(11)-BNC through degradation of the carboxyl group in the 20-position and its replacement by a nitrogen function into C21-steroid compounds which in turn represent valuable intermediate products for the production of pharmacologically active steroid derivatives.

DESCRIPTION OF THE INVENTION

In a first embodiment, therefore, the present invention relates to a process for the production of Δ4-C-21-steroid compounds with a nitrogen function in the 20-position and optionally containing at least one other double bond in the 1(2)- and/or 9(11)-position corresponding to general formula I below:

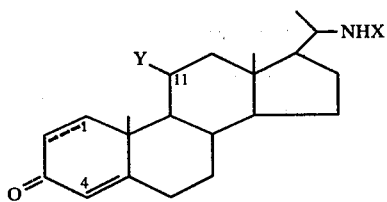

(I)

in which Y represents hydrogen, a hydroxyl group or, together with the C-atom substituted by Y, a carbonyl group or may even be replaced by a 9(11)-ene bond and in which X represents hydrogen, acyl, a carbonic acid ester residue or, together with the adjacent hydrogen atom on the nitrogen, a carbonyl group. The process according to the invention is characterized in that the C-20-carboxylic acid halide structurally analogous to the required reaction product and corresponding to general formula II below

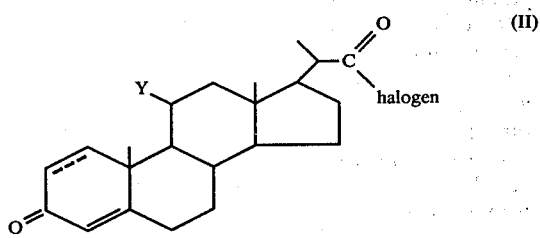

(II)

in which Y is as defined above and halogen preferably represents chlorine or bromine, is converted into the corresponding carboxylic acid acid azide which is (a) either transfored into the C-20-isocyanate through the elimination of nitrogen and the C-20-isocyanate thus obtained is if desired converted into the C-20-carbamate and/or the C-20-amine (b) or directly transformed into the C-20-amine.

The individual stages and possible degradation steps of the process according to the invention are diagrammatically illustrated in formula scheme III and are described in detail in the following. In the interests of simplicity, formula scheme III shows only the side chain substituents in the 17-position of the steroid ring skeleton.

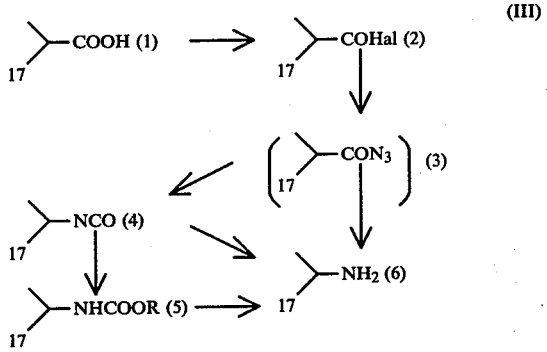

(III)

More particularly, the various stages of the process according to the invention are carried out as follows:

Transformation of the 20-carboxylic acid compound (1) into the corresponding carboxylic acid halide (2)

The conversion of carboxylic acids into acid halides, particularly acid chlorides, using the halogenating agents, such as phosphorus halides, oxalyl halide or, in particular, thionyl halide is a reaction which has long been known per se and generally used, even in the series of 20-carboxy-pregnane derivatives.

However, if the reaction conditions described in the literature for the reaction of 3-acetoxy-bis-norcholenic acid with thionyl chloride (cf. for example FIAT Final Report No. 996, pages 24 et seq, and also P. L. Julian, E. W. Meyer and H. C. Printyl, J. Am. Chem. Soc. 70, 887 (1948) are applied for example to Δ1,4-BNC and if the acid chloride thus obtained is subsequently esterified with methanol and the crude product analyzed, the gas chromatogram shows an additional peak whilst elemental analysis reveals a distinct, initially unexpected Cl-content.

The same applies to an even greater extent where oxalyl chloride is used instead of thionyl chloride.

The reason for the occurrence of these unwanted impurities which distinctly reduce the yield of required product and which can give rise to purification problems in further reactions involving the acid chloride probably lies in chlorination, optionally followed by aromatization, of the A-ring in the steroid skeleton, as known for example for the reaction of androsta-1,4-diene-3,17-dione (ADD) with oxalyl chloride, c.f. G. W. Moersche et al., J. Org. Chemistry, 29, 2495 (1964).

Surprisingly, the acid halides required in accordance with the invention are formed under such mild reaction conditions that there is no undesirable co-reaction of other reactive sites of the parent monounsaturated or polyunsaturated BNC-structure. Thus, it has surprisingly been found that, for example, substantially quantitative acid chloride formation takes place when the following reaction conditions are applied: reaction temperatures below 15° C., preferably below 5° C. and, more particularly, in the range from 0° to 5° C., stoichiometric quantities of the reactants or only a very slight excess of the halogenating agent which preferably amounts to no more than 20 mole percent and, more particularly, to no more than 10 mole percent and working in the presence of an inert diluent, if desired in the presence of small quantities of a basic catalyst.

Suitable inert solvents are, for example, halogenated hydrocarbons or, with limitations, ethers. Suitable inert solvents are, for example, methylene chloride or chloroform. Suitable halogenating agents are phosphorus halides, particularly $PCl_3$ or $PCl_5$, and the corresponding bromides, but above all thionyl halide, particularly thionyl chloride. Catalytic quantities of a base, particularly pyridine or dimethyl formamide, accelerate the reaction, for example in the case of Δ4-BNC, but in many cases are unnecessary. The presence of a catalyst may be desirable in individual cases.

Depending on the other process parameters and on the compounds to be reacted with one another, individual process parameters may even lie beyond the limits hitherto quoted. Thus, the process temperature for example may be in the range from about −20° C. to about 75° C. provided that, at the higher temperatures of this range, the formation of undesirable ring halogenation products is avoided by suitably controlling the process. The quantity in which the halogenating agent is used may also considerably exceed the stoichiometrically necessary quantity, again with the proviso that the other process conditions are suitably adapted. Thus, for example, quantities of up to 5 equivalents and preferably up to 3 equivalents of the halogenating agent may be used in special cases. The reaction is usually carried out at normal pressure. The halogenating agent is best added to a solution of the steroid compound to be reacted in the inert solvent. It has proved to be of advantage to use the halogenating agent in the purest possible form. Impurities normally present in the halogenating agent evidently promote undesirable secondary reactions. For example, it is advisable to purify the halogenating agent with an unsaturated compound, such as linseed oil or, more particularly, squalene. These unsaturated components react with the impurities in the halogenating agent and thus reduce the formation of undesirable secondary products to a minimum. In the production of 11-hydroxylated acid halides, an excess of the halogenating agent should be avoided.

Conversion of the acid halide (2) into the azide (3)

The comprehensive disclosures in the literature which describe the reaction of carboxylic halides with azides, particularly in conjunction with the Curtius degradation of carboxylic acids through their azides to the next lowest primary amines in the first stage, apply in principle here.

The carboxylic acid azides are generally formed in a smooth reaction, cf. for example Houben-Weyl "Methoden der organischen Chemie" (1957), Vol. XI/1, pages 862 et seq, particularly page 864.

The modified variant of the Curtius degradation using the two-phase technique, as described in German Offenlegungsschrift No. 22 45 611 for the degradation of fatty acids and dimerized fatty acids, has proved to be particularly effective for the purposes of the invention. The two-phase technique on which this variant is based is characterized in that the acid halide is dissolved in an organic solvent substantially immiscible with water and the reaction of the acyl halide and the metal azide is carried out as a two-phase reaction with an aqueous solution of the azide in the presence of a quaternary ammonium salt as phase transfer catalyst.

This stage of the process according to the invention is preferably carried out under conditions which preclude substantial degradation of the acyl azide formed to the isocyanate. It is preferably carried out at temperatures below about 25° C., more particularly at temperatures below about 15° C. and best at temperatures in the range from about 0° to 15° C. The reactants are preferably moved, for example stirred, during the reaction. However, the mixing effect thus generated should not lead to the formation of a stable emulsion. On completion of the reaction, the organic solution containing the acyl azide may be separated off from the aqueous phase. The organic phase is washed.

Suitable water-immiscible solvents are, for example, aliphatic, alicyclic or aromatic hydrocarbons or, in particular, halogenated hydrocarbons, such as methylene chloride or chlorobenzene. The concentration of the acyl halide in the solvent is not critical and may amount for example to between about 5 and 50% by weight. The metal azides used are preferably alkali metal or alkaline-earth metal azides, particularly potassium azide and, above all, sodium azide. The quaternary ammonium salt contains four organic radicals of any type, for example alkyl or aryl radicals, on the nitrogen. The total number of carbon atoms is preferably no more than about 30. Corresponding quaternary salts containing up to about 20 carbon atoms in the residues alkylating the nitrogen atom may be particularly suitable. Short-chain alkyl radicals containing from 1 to 5 carbon atoms may be particularly preferred. Radicals of any type may be present as the anion. Halide ions may be particularly appropriate. The quaternary ammonium salt is normally used in only small quantities, for example in quantities of from 0.01 to 10 equivalent percent, based on the acid halide. The preferred process temperatures are below about 10° C. and, more particularly, in the range from 0° to 5° C.

After the reaction is over and after the organic phase has been separated off and washed to reduce the content of quaternary ammonium compound, the steroid-20-carboxylic acid azide formed may be isolated by carefully removing the solvent. In most cases, however, the solution of the acid azide is directly further processed by one of the methods described in the following.

Conversion of the acid azide (3) to the isocyanate (4) by elimination of nitrogen Thermal decomposition of the dry solution of the acid azide in the solvent, preferably at decomposition temperatures above 20° C., leads to the isocyanate with elimination of nitrogen and rearrangement of the molecule. The reaction involved here is one of the steps of the classical Curtius degradation (cf. Houben-Weyl loc. cit., particularly pages 862 and 865/866). The thermal decomposition process is carried out under optionally increasing temperatures until the evolution of nitrogen is substantially over. The isocyanate formed may be isolated, although it may also be directly used as a crude product for its further reactions.

Transformation of the isocyanates (4) into the carbamates (5) and the amines (6)

The general principles of the Curtius degradation (cf. Houben-Weyl loc. cit., particularly pages 865/866) apply here as well. The reaction of the isocyanates with alcohols gives the corresponding carbamates (5). Suitable alcohols are any saturated, unsaturated, aromatic, straight-chain and branched-chain alcohols. The hydrocarbon radical of the alcohol should be preferably contain no more than 20 carbon atoms and, more particularly, no more than 10 carbon atoms. Particularly suitable simple representatives are lower alkanols, for example the $C_1$ to $C_4$-alcohols.

The carbamates (5) may be transformed into the amines (6) by hydrolysis. However, the Δ1,4-compounds are less suitable for this stage of the process because the A-ring of the steroid system is in danger of being attacked under the highly acid conditions under which hydrolysis is carried out, for example in strong hydrochloric acid.

The isocyanates (4) may be directly converted into the amines (6) by preferably aqueous acid decomposition with decarboxylation. The reaction medium used for this stage of the process may be for example an aqueous carboxylic acid, particularly aqueous acetic acid. In the final step, the amine may be released from the amine salt formed by treatment with bases, for example alkali hydroxide, and isolated.

Direct transformation of the azide (3) into the amine (6)

The carboxylic acid azide (3) may be directly transformed into the C20-amine (6) in a particularly simple reaction. It is known that carboxylic acid azides may be directly degraded to the amines by heating with aqueous acids, particularly aqueous acetic acid. In this case, too, the free amines may be released from the amine salts initially formed by reaction with strong bases, particularly alkali hydroxide (cf once again Houben-Weyl loc. cit., particularly pages 870/871). More particularly, it is possible for example to adopt the following procedure:

The solution of the acid azide formed in the water-immiscible solvent is added dropwise to an excess of aqueous acetic acid (concentration for example 50 to 80% by weight). At the same time, the solvent is carefully distilled off from the reaction mixture. In some cases, it may be advisable to replace the water removed together with the solvent. Finally, the reaction temperature is increased to 60°-70° C. Once the evolution of gas has abated, the mixture is subjected to steam distillation. The residue is concentrated in vacuo. Water-immiscible solvents and aqueous alkali liquor are added and the mixture is stirred. After subsequent phase separation, the organic phase is washed with water and, finally, concentrated to dryness. The crude amine which accumulates in the form of a crystaline solid may be used, generally without further purification, for transformation of the amino group into a carbonyl group. Preferably, in this case, the procedures disclosed in U.S. Pat. No. 4,252,732 are followed.

Of the compounds to be produced in accordance with the invention, the derivatives of Δ1,4,9(11)-BNC corresponding to general formula I inter alia are new compounds and, as such, fall within the scope of the present invention. In particular, therefore, the present invention relates to pregna-1,4,9(11)-triene-3-one-20-amine and to the corresponding compounds containing the isocyanate group and the carbamate group in the 20-position.

The steroid compounds containing an oxygen function in the 11-position which may be obtained in accordance with the invention are also new.

In another embodiment, therefore, the present invention relates to new C21-steroid compounds containing an oxygen function in the 11-position and a nitrogen function in the 20-position and corresponding to general formula IV below:

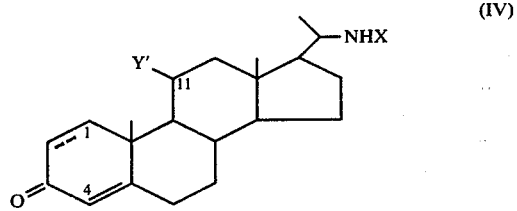

(IV)

in which Y' is a hydroxyl group or, together with the C-atom substituted by Y', represents a carbonyl group and X represents hydrogen, acyl, preferably a hydrocarbon acyl having up to 20 carbon atoms, a carbonic acid ester radical preferably carbonyloxy-lower alkyl, or, together with the adjacent hydrogen atom on the nitrogen, represents a carbonyl group.

The new compounds according to the invention may be unsaturated once in the A-ring of the steroid skeleton (Δ4-compounds), although they may also be unsaturated twice (Δ1,4-compounds). Compounds of this second type can be particularly valuable. The following description relates in particular to these Δ1,4-compounds, although the invention is by no means limited thereto.

A feature which all these new compounds have in common is their oxygen function in the 11-position and their nitrogen function in the 20-position.

The oxygen function in the 11position may be either a hydroxyl group or a carbonyl group which is formed together with the C-atom substituted by the oxygen in the 11-position. The possibilities of the α-position and β-position are available for the hydroxyl group in the 11-position. Both types of compound fall within the scope of the present invention. The β-hydroxyl compounds may be of particular significance for the reasons mentioned above.

The above-mentioned possibilities are available for the nitrogen function in the 20-position. If X in general formula IV above represents hydrogen, the amino group —NH$_2$ is present in the 20-position. This amino group may be present in the 20α-configuration or in the 20β-configuration. Both types of position isomers fall within the scope of the present invention. For preparative reasons, the α-position may be particularly significant in this case.

The 20-amino compounds may readily be transformed into corresponding acyl amido compounds by acylation. In this case, X in formula IV represents the residue RCO— where R may be a hydrocarbon radical. These reaction products are also new compounds and fall within the scope of the present invention.

Another group of new compounds according to the invention are the 20-carbamate compounds, i.e. compounds corresponding to general formula IV in which X represents a carbonic acid ester residue. The structural isomerisms (20α- and 20β-position) mentioned for the 20-amino compounds apply both to these 20-carbamate derivatives and also to the above-mentioned acylamido compounds.

Finally, the invention relates to 20-isocyanato-derivatives corresponding to general formula IV. In this case, therefore, the isocyanate group —NCO is present in the 20-position, i.e. X in the general formula represents the CO-group together with the adjacent hydrogen on the nitrogen.

In all the cases discussed here, the A-ring of the steroid skeleton may be unsaturated once (Δ4) or twice (Δ1,4). For all types, Y may have the various meanings indicated above.

One particularly preferred class of the new compounds according to the invention are the 20-amino-pregna-1,4-diene-3-one compounds corresponding to general formula V below:

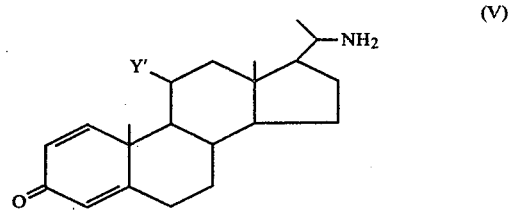

(V)

in which Y' is a hydroxyl group, particularly the β-hydroxyl group, or together with the C-atom substituted by Y' represents a carbonyl group. The corresponding Δ4-compound also falls into this class of particularly preferred compounds according to the invention. More particularly all of the compounds having the formula I,X═H:

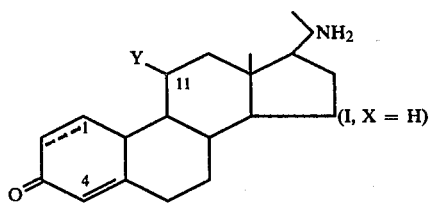

including the novel compounds of formula IV, X=H are useful intermediate products for the production of steroid compounds having the acetyl side chain of progesterone in accordance with the following scheme:

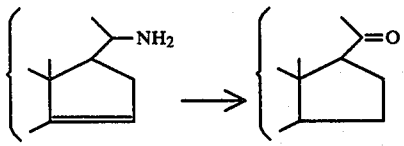

The method described in U.S. Pat. No. 4,252,732 for converting the 20-amino group to the 20-oxo group can be followed in all instances. The method described by patentee in Example 1 can also be applied to the novel compounds of formula IV, X=H, which have an oxygenated function in the 11-position. For example, by following the process of Example 1 of the patent, 20-amino-pregna-1,4-dien-3,11-dione will give the known compound pregna-1,4-dien-3,11,20-trione, and 20-amino-11β-hydroxy-pregna-1,4-dien-3-one will give the known compound pregna-1,4-dien-11β-ol-3,20-dione. Both these 20-keto compounds are described in U.S. Pat. No. 2,128,238.

The conversion of the 20-amine to the 20-keto effected by the agency of 3,5-di-tert.-butyl-o-benzoquinone according to Example 1 of 4,252,732 can be applied to the above compounds of formula I, X=H.

The above specifically mentioned keto compounds, as well as other keto compounds derived from compounds of formula IV, X=H can be transformed, in analogy to the process of Hogg et al., J. Am. Chem. Soc. 77, 4438 (1955) into 17(20)-en-21-carboxylated steroids

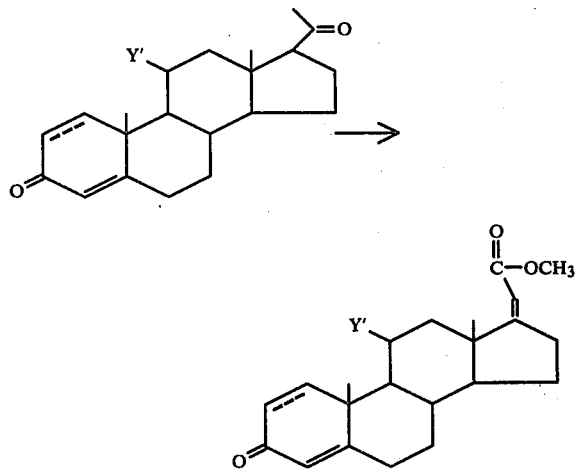

By the above process, pregna-1,4-dien-3,11,20-trione will give the methyl ester of 3,11-dioxo-prenga-1,4,17(20-trien-21-carboxylic acid and pregna-1,4-dien-11β-ol-3,20-dione will give the methyl ester of 11β-hydroxy-3-oxo-pregna-1,4,17(20)-triene-21-carboxylic acid.

The further transformation of the 17(20) unsaturated esters, via the respective 21-hydroxy-pregnane derivatives into corticoids such as prednisone and prednisolone has likewise been described by Hogg et al, J. Am. Chem. Soc. 77, 4438 (1955) according to the following reaction schema.

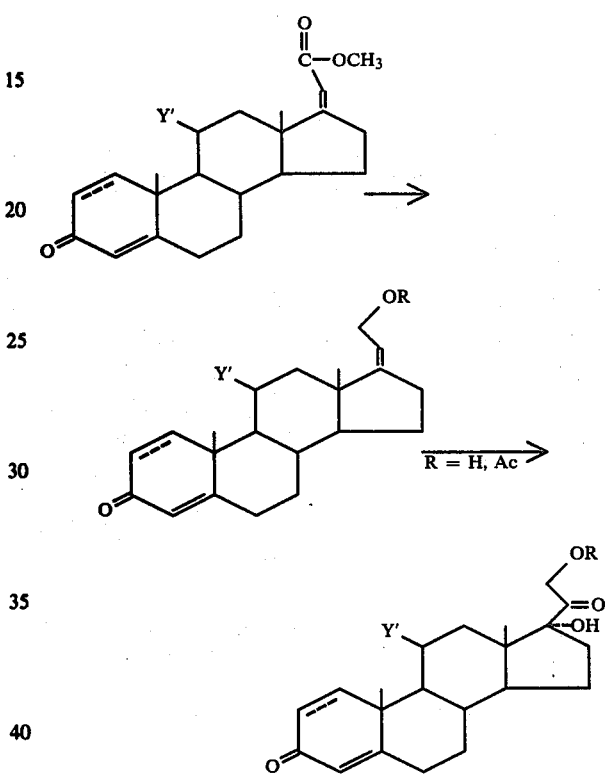

An improved reduction step for the above reaction is described in my commonly assigned U.S. Patent Application Ser. No. 262,969, filed May 12, 1981, now U.S. Pat. No. 4,370,271.

Thus, according to the claimed method, access is opened up to intermediate products for pharmacologically effective corticoids such as prednisone and prednisolone.

The likewise new 20-isocyanato-pregna-1,4-diene-3-one derivatives and the 20-carbamate derivatives derived therefrom

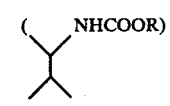

are to be regarded as preliminary stages for the 20-amino compounds. A method for the hydrolysis of steroid carbamates is described in U.S. Pat. No. 4,252,730.

Particularly important representatives of the subclass of novel compounds according to the invention are, for example, 20-amino-pregna-1,4-diene-3,11-dione and 20-amino-11β-hydroxy-pregna-1,4-diene-3-one.

The 20-isocyanato-pregna-1,4-diene-3-one compounds according to the invention correspond to general formula VI below:

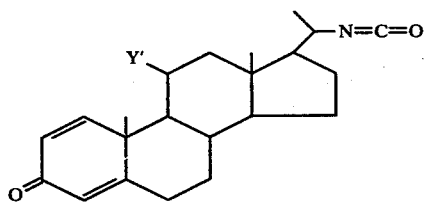

in which Y' is again a hydroxyl group, preferably the β-hydroxyl group, or together with the C-atom substituted by Y' in the 11-position, represents a carbonyl group. Corresponding Δ4-isocyanato compounds count as important compounds according to the invention. Particularly interesting examples of this class of compounds are 20-isocyanato-pregna-1,4-diene-3,11-dione and 20-isocyanato-11β-hydroxy-pregna-1,4-diene-3-one.

The 20-isocyanato compounds are in turn the starting point for the corresponding carbamic acid derivatives which may readily be obtained in known manner by the addition of alcohols onto the isocyanate group.

The corresponding 20-carbamato-pregna-1,4-diene-3-one compounds correspond to general formula VII below:

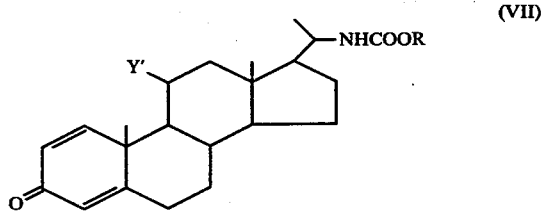

in which Y' is again a hydroxyl group, particularly the β-hydroxyl group, or together with the C-atom substituted by Y' in the 11-position represents a carbonyl group. Characteristic representatives of this class of compounds are 20-carbamato-pregna-1,4-diene-3,11-dione and 20-carbamato-11β-hydroxy-pregna-1,4-diene-3-one.

If X in general formula I represents RCO—, R may be a hydrocarbon group. The radical in question is normally an alkyl, aryl, alkaryl or aralkyl radical. This radical preferably contains no more than 20 carbon atoms and, more particularly, no more than 10 carbon atoms. Corresponding straight-chain or branched-chain alkyl radicals containing up to 5 carbon atoms and aryl radicals having an aromatic ring or corresponding alkaryl or alkyl radicals may be particularly preferred. The acetyl radical is a particularly suitable radical for identifying the compounds.

The steroid compounds obtainable in accordance with the invention are thus valuable products of steroid chemistry. They are particularly suitable for further chemical transformations on the substituent in the 17-position and/or on the steroid ring skeleton, as has been described. For example, known pharmacologically active compounds may be conveniently obtained in this way.

The following examples are illustrative of the invention without being limitative in any respect.

EXAMPLE 1

20-amino-pregna-1,4-dien-3,11-dione (a) 0.25 ml of thionyl chloride freshly distilled over squalene and 1 drop of pyridine are added at 0° C. to 1 g of 1,4-oxo-BNC in 20 ml of dry methylene chloride, followed by stirring for 70 minutes. $CH_2Cl_2$ and excess $SOCl_2$ are then removed in vacuo at 0° C. 5 ml of absolute $CH_2Cl_2$ are added to the residue, followed by reconcentration to dryness, leaving 1 g of the carboxylic acid chloride as residue.

(b) The acid chloride is dissolved in 20 ml of dry methylene chloride, a solution of 273 mg of sodium azide in 3 ml of water and 10 mg of tetrabutyl ammonium chloride as phase transfer catalyst are added at a temperature below 10° C. and the mixture stirred for 30 minutes. The aqueous phase is then separated off and the $CH_2Cl_2$-phase is washed twice with a little water at a temperature below 10° C.

(c) A solution of the carboxylic acid azide in $CH_2Cl_2$ is added to 25 ml of 70% acetic acid, followed by slow heating until $CH_2Cl_2$ distills off. An evolution of gas is observed on heating. After most of the methylene chloride has distilled off, the mixture is kept at around 60° C. for another hour. The reaction mixture is then diluted with 20 ml of water and concentrated in vacuo in a rotary evaporator.

The greasy residue is taken up in methylene chloride, an excess of 0.5 N sodium hydroxide is added and the mixture stirred overnight. The phases are then separated, the organic phase is washed with water, dried ($Na_2SO_4$) and concentrated to dryness. Yield: 850 mg (92%) of crude amine.

IR (KBr): 1700 (11-oxo), 1663 (3-oxo), 1618 and 1600 (1(2) and 4(5)-double bond) $cm^{-1}$.

EXAMPLE 2

20-acetamido-pregna-1,4-dien-3,11-dione 0.3 ml of acetanhydride, 0.33 ml of triethylamine and 5 to 10 mg of 4-(N,N-dimethylamino)-pyridine are added at room temperature to 500 mg of the amine produced in accordance with Example 1 in 10 ml of absolute $CH_2Cl_2$. After 2 hours, a thin-layer chromatogram (silica gel; $CH_2Cl_2$/ethyl acetate/$CH_3OH$ 5:4:1) shows that the reaction is complete. The reaction mixture is successively washed with cold 2 N HCl, $NaHCO_3$-solution and water, dried over $Na_2SO_4$ and concentrated to dryness, leaving as residue 460 mg of the product which, according to thin-layer chromatography, contains very few impurities.

For further purification, the product was first digested with ether, after which a small quantity of the white crystalline product obtained was subjected to fine purification by preparative high-pressure liquid chromatography.

M.p. (after dissolution and reprecipitation from isopropanol/ether): 195°–202° C.

$C_{23}H_{31}NO_3$ observed: C: 74.35%; H: 8.18%; N: 3.62%; calculated: C: 74.76%; H: 8.46%; N: 3.79%.

EXAMPLE 3

20-amino-11β-hydroxy-pregna-1,4-dien-3-one

The reaction was carried out in the same way as described in Example 1 for the preparation of the corresponding 11-oxo-amine. Yield: from 1 g of Δ1,4-11β-

OH-BNC II, 785 mg (85%) of crude, crystalline product of the required constitution.

IR (KBr): 1660 (3-oxo), 1618 and 1600 (1(2)- and 4(5)-double bond) cm$^{-1}$.

EXAMPLE 4

20-acetamido-11$\beta$-hydroxy-pregna-1,4-dien-3-one 500 mg of the amine of Example 3 were reacted in the same way as described in Example 2 except that, to avoid acetylation of the 11$\beta$-OH-group, pyridine was used instead of triethylamine/dimethyl aminopyridine. Working up and isolation were also carried out in the same way as in Example 2.

The residue left after removal of the solvent crystallised after treatment with ether. Yield: 465 mg of the product which, according to analysis by thin-layer chromatography, contains very few impurities.

Fine purification was again carried out by preparative high-pressure liquid chromatography.

M.p. (after recrystallization from isopropanol): 271°–278° C. (decomp); some browning beyond only 264° C.

$C_{23}H_{33}NO_3$ observed: C: 74.13%; H: 8.70%; N: 3.65%; calculated: C: 74.36%; H: 8.95%; N: 3.77%.

EXAMPLE 5

20-methyl carbamato-11$\beta$-hydroxy-pregna-1,4-dien-3,11-dione (a) A solution of the acid azide in methylene chloride is prepared from 1 g of $\Delta$1,4-oxo-BNC in accordance with Example 1, paragraphs (a) and (b). The solution thus prepared was dried over molecular sieve 4A and left standing overnight. Thereafter, an IR-spectrum shows that rearrangement to the isocyanate is complete (as evidenced by the isocyanate band at 2260 cm$^{-1}$).

IR-data for 20-isocyanato-pregna-1,4-diene-3,11-dione (in $CH_2Cl_2$); 2260, 1708, 1662, 1622, 1602 cm$^{-1}$ (b) After removal of the drying agent, some of the $CH_2Cl_2$ is distilled off, after which 15 ml of absolute methanol are added and the remaining $CH_2Cl_2$ is distilled off. After a total reaction time of 4 hours, ultimately in boiling methanol, a thin-layer chromatogram shows that the reaction is over. Concentration to dryness gives 920 mg of a yellowish-white crystalline solid. The thin-layer chromatogram shows only small quantities of impurities. Approximately 100 mg of this substance were purified first by preparative thin-layer chromatography (2 mm silica gel, toluene/butanone 60:40) and then by recrystallization from isopropanol.

M.p. (after recrystallization from isopropanol): 188°–192° C.

$C_{23}H_{31}NO_4$ observed: C: 71.95%; H: 7.92%; N: 3.52%; calcuiated: C: 71.66%; H: 8.11%; N: 3.63%.

EXAMPLE 6

20-methyl carbamato-11$\beta$-hydroxy-pregna-1,4-dien-3-one (a) 20-isocyanato-11$\beta$-hydroxy-pregna-1,4-diene-3-one was prepared from $\Delta$1,4-11-OH-BNC in the same way as described in Example 5, paragraph (a).

IR (in $CH_2Cl_2$): 2262, 1660, 1620, 1601 cm$^{-1}$.

(b) Further reaction to form the 11$\beta$-OH-methyl carbamate was carried out in the same way as described in Example 5, paragraph (b) for the corresponding 11-oxo-compound. 820 mg of crude carbamate were obtained from 1 g of $\Delta$1,4-11$\beta$-OH-BNC.

M.p. (after dissolution and reprecipitation from isopropanol/ether): the substance melted at 148° C., crystallized out on further heating (~150°–160° C.) and finally melted at 220° to 224° C.

$C_{23}H_{33}NO_4$ observed: C: 71.41% H: 8.35%; N: 3.48%; calculated: C: 71.29%; H: 8.58%; N: 3.61%.

EXAMPLE 7

Production of 20-amino-pregna-1,4-dien-3-one (a) Pregna-1,4-dien-3-one-20-carbonyl chloride:

4.0 ml (55 mMoles) of thionyl chloride freshly distilled over squalene are added at 0° C. to 17 g (50 mMoles) of $\Delta$1,4-BNC (1) in 100 ml of absolute $CH_2Cl_2$, followed by stirring for 20 minutes at 0° C. The solvent and excess thionyl chloride are then removed in vacuo at the same temperature. The residue is again taken up in methylene chloride and the solution again concentrated to dryness. The residue may be used for further reactions. To obtain an acid chloride suitable for analysis, the crude acid chloride is digested with absolute ether and dried after the ether has been carefully distilled off in an oil pump vacuum.

|  |  | Observed | Calculated |
|---|---|---|---|
| Elemental Analysis: | C | 73.0/72.9 | 73.2 |
|  | H | 8.01/7.95 | 8.10 |
|  | Cl | 9.72/9.51 | 9.82 |

Chloride determination after hydrolysis of a sample revealed 9.75% of chlorine expressed as Cl (calculated 9.82%).

M.p. (of the crude acid chloride: 142° C. decomposition after sintering at 135°–138° C.

(b) The acid chloride (2) is produced from 25 g of $\Delta$1,4-BNC (1) in accordance with (a) and dissolved in 150–200 ml of absolute $CH_2Cl_2$. 5.8 g of sodium azide in approximately 15 ml of water and 150 mg of tetrabutyl ammonium chloride as phase transfer catalyst are added to the resulting solution at 0° C. After stirring for 20 minutes at 0° C., 20 ml of ice water are added, the phases are separated and washed with a little ice water.

A solution of the acid azide (3) in $CH_2Cl_2$ is added dropwise to approximately 300–350 ml of 70% acetic acid. At the same time, methylene chloride is carefully distilled off from the reaction mixture. (It is advisable in some cases to replace the water removed together with the methylene chloride.) Finally, the reaction temperature is increased to 60°–70° C. (0.5–1 h), hafter which the mixture is subjected to steam distillation until approximately 600 to 800 ml of distillate have passed over and the residue is largely concentrated in vacuo.

Approximately 200 ml of $CH_2Cl_2$ and 200 ml of 10% sodium hydroxide solution are then added to the residue thus concentrated, followed by stirring overnight.

After phase separation, the organic phase is washed with water, dried and finally concentrated to dryness.

This leaves 21.8 g of a crystalline solid containing 90% of 20-amino-pregna-1,4-dien-3-one (6). The crude amine may be used without further purification for conversion into dehydroprogesterone, following the process of Example 1 of U.S. Pat. No. 4,252,732.

EXAMPLE 8

Degradation of $\Delta$1,4-BNC to the corresponding isocyanate 20-isocyanato-pregna-1,4-dien-3-one A solution of the acid azide (3) is prepared in accordance with Example 7b from 25 g of $\Delta$1,4-BNC. The methylene chloride solution of the acid azide (3) is dried over sodium sulfate. A slow evolution of N₂ is indicative of rearrangement into the isocyanate. This rearrangement may be observed by IR-spectroscopy: The isocyanate band at 2270 cm⁻¹ intensifies at the same rate as the azide band at 2120 cm⁻¹ weakens. Even at +4° C., rearrangement is complete after 24 hours. As expected, it is accelerated by careful heating.

Concentration in vacuo gives 23.4 g of a solid, pale yellow product of which more than 90 percent consists of the isocyanate (IR (CH₂Cl₂): 2270, 1662, 1621, 1620 cm⁻¹). (The isocyanate (4) may be converted into 20-aminopregna-1,4-dien-3-one in the same way as described in Example 7b for the solution of the acid azide (3).)

EXAMPLE 9

Preparation of the methyl carbamate (5), R=CH₃, from 20-isocyanato-pregna-1,4-dien-3-one A solution of 20-isocyanato-pregna-1,4-dien-3-one is prepared from 17 g of Δ-1,4-BNC in the same way as described in Examples 7a and 7b. 80 ml of abs. CH₃OH are added thereto, CH₂Cl₂ is distilled off through a short column and the mixture subsequently refluxed for 6 to 8 hours. The progress of the reaction may be observed from the weakening of the isocyanate band at 2270 cm⁻¹.

Removal of the methanol by distillation in vacuo leaves 16.4 g of a crystalline residue which is almost pure methyl carbamate according to analysis by thin-layer chromatography and to spectroscopic data.

¹H-NMR (80 MHz, CDCl₃, δ-values): 0.78 ppm, s (18—CH₃), 1.23 ppm, s (19—CH₃), 1.15 ppm, d (J=9 Hz) (21—CH₃), 3.64 ppm, s (0—CH₃), 3.64 ppm, m (20—CH), olefinic protons with lines between 6.06 and 7.1 ppm)

EXAMPLE 10

Preparation of 20-amino-pregna-4-dien-3-one from Δ4-BNC 3.49 ml of SOCl₂ freshly distilled over squalene and 5 drops of pyridine are added at 0° C. to 10 g of Δ4-BNC in 80 ml of abs. CH₂Cl₂. After stirring for 2 hours 0° C. the solvent is removed in vacuo along with SO₂, HCl and excess thionyl chloride. The residue is taken up in a little dry CH₂Cl₂ and reconcentrated to dryness. The solid acid chloride is dissolved in 100 ml of abs. CH₂Cl₂ and the resulting solution subjected to the Curtius degradation by the method described in Example 2. 7.6 g of crystalline crude product containing 80% of 20-amino-pregna-4-dien-3-one are ultimately obtained.

EXAMPLE 11

Preparation of 20-amino-pregna-1,4,9(11)-trien-3-one 2.1 ml of dry pyridine and 4.2 ml of thionyl chloride freshly distilled over squalene are added at 0° C. to 5 g of 11β-hydroxy-pregna-1,4-dien-3-one-20-carboxylic acid in 125 ml of dry CH₂Cl₂. After stirring for 1 hour at 0° C., the solvent is removed in vacuo along with SO₂, HCl and excess thionyl chloride. The residue is taken up in 50 ml of CH₂Cl₂ and reconcentrated to dryness. Apart from pyridine, HCl, the residue consists above of all of pregna-1,4,9(11)-trien-3-one-20-carbonyl chloride.

The acid chloride thus obtained is dissolved in 125 ml of CH₂Cl₂, the resulting solution is washed once at 0° C. with a little cold water and then subjected to the Curtius degradation by the method described in Example 2 for pregna-1,4-dien-3-one-20-carbonyl chloride. Crude 20-amino-pregna-1,4,9(11)-trien-3-one is obtained in a yield of 3.81 g.

Identification and confirmation of structure are best carried out after acetylation of the NH₂-group (cf. Example 12).

EXAMPLE 12

20-acetamido-pregna-1,4,9(11)-trien-3-one 2 g of the amine produced in accordance with Example 11 were dissolved without further purification in 50 ml of dry methylene chloride. 2 ml of acetanhydride, 2.94 ml of triethyl amine and a catalytic quantity of 4-dimethylaminopyridine were added to the resulting solution. The reaction mixture was successively washed with 2n H₂SO₄, 5% KHCO₃-solution and water, subsequently dried over Na₂SO₄ and finally concentrated dryness.

2 g of the expected acetamide are obtained. The ¹H-NMR-spectrum confirms the presence of the postulated structure. The crude product is substantially pure.

¹H-NMR (CDCl₃, 80 MHz, δ-values): 0.74 s (18—CH₃); 1.40 s (19—CH₃), 1.13 d (J=6.3 Hz) (21—CH₃), 1.95 s (OCH₃), 5.50 (11—CH) ABC-system of 1—CH, 2CH, 4CH with lines at 6.05, 6.18, 6.20, 6.31, 6.33, 7.13, 7.25.

The preceding specific embodiments are illustrative of the practice of the invention. It is to be understood however, that other expedients known to those skilled in the art or disclosed herein, may be employed without departing from the spirit of the invention or the scope of the appended claims.

I claim:

1. A process for the production of Δ4-C21-steroid compounds with an amine in the 20-position corresponding to general formula I:

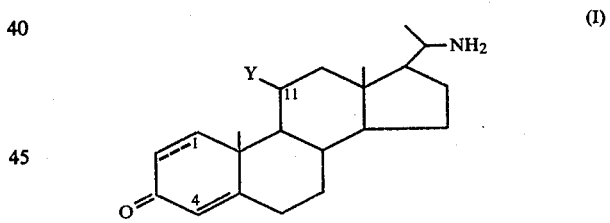

in which Y is a member selected from the group consisting of hydrogen, hydroxyl, and together with the C-atom substituted by Y, a carbonyl and a 9(11)-ene bond characterized in that a C20-carboxylic acid halide corresponding to general formula II:

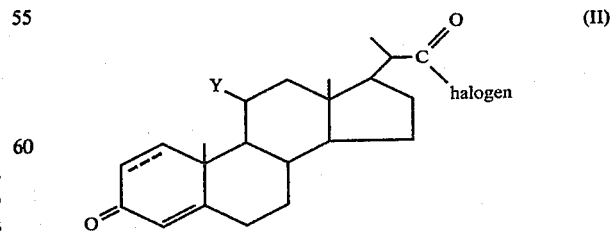

in which Y is defined above, is reacted with a metal azide in an aqueous/organic two-phase reaction at a temperature of below about 25° C., the resulting carboxylic acid azide is recovered and heated to give the corresponding C20-isocyanate by the elimination of nitrogen and the corresponding C20-isocyanate thus obtained is coverted into the C20-amine, and recovering said Δ4-C21-steroid compounds.

2. A process as claimed in claim 1, characterized in that the reaction of the C20-carboxylic acid halide to form the corresponding azide is carried out using quaternary ammonium salts as phase transfer catalysts.

3. A process as claimed in claim 2 in which a reaction temperature of from 0° to 5° C. is utilized.

4. C21-steroid compounds with an oxygen function in the 11-position and a nitrogen function in the 20-position corresponding to general formula IV:

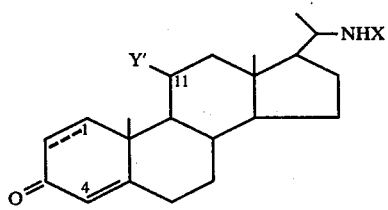
(IV)

in which Y' is a member selected from the group consisting of hydroxyl and, together with the C-atom substituted by Y', a carbonyl and X is a member selected from the group consisting of hydrogen, acetyl, carbonyloxy-lower alkyl and, together with the adjacent hydrogen atom on the nitrogen, a carbonyl.

5. 20-amino-pregna-1,4-dien-3-one compounds corresponding to formula V:

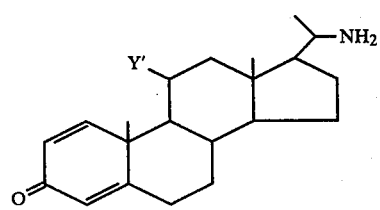
(V)

in which Y' is a member selected from the group consisting of hydroxyl, particularly β-hydroxyl and, together with the C-atom substituted by Y' a carbonyl.

6. The compound of claim 5 being 20-amino-pregna-1,4-dien-3,11-dione.

7. The compound of claim 5 being 20-amino-11β-hydroxy-pregna-1,4-dien-3-one.

8. 20-isocyanate-pregna-1,4-dien-3-one compounds corresponding to formula VI:

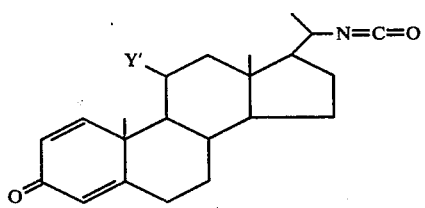
(VI)

in which Y' has the meanings as defined in claim 5.

9. The compound of claim 8 being 20-isocyanato-pregna-1,4-dien-3-11-dione.

10. The compound of claim 8 being 20-isocyanato-11β-hydroxy-pregna-1,4-dien-3-one.

11. 20-carbamato-pregna-1,4-dien-3-one compounds corresponding to formula VII:

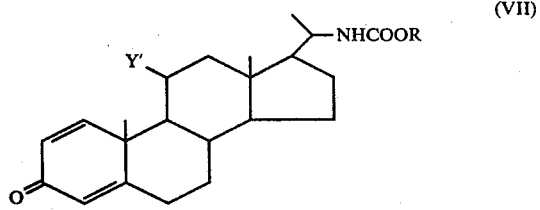
(VII)

in which Y' is as defined in claim 5 and R represents a lower alkyl.

12. The compound of claim 11 being 20-carbamatomethyl pregna-1,4-dien-3,11-dione.

13. The compound of claim 11 being 20-carbamatomethyl-11β-hydroxy-pregna-1,4-dien-3-one.

14. Pregna-1,4,9(11)-trien-3-one-20-amine.

15. Pregna-1,4,9(11)-trien-3-one-20-isocyanate.

16. A process for the production of Δ4-C21-steroid compounds with an amine in the 20-position corresponding to general formula I:

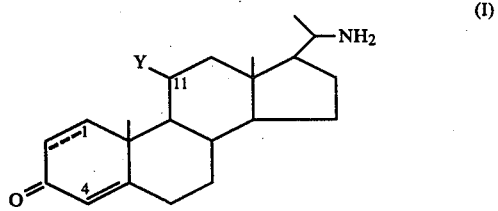
(I)

in which Y is a member selected from the group consisting of hydrogen, hydroxyl, and together with the C-atom substituted by Y, a carbonyl and a 9(11)-ene bond characterized in that a C20-carboxylic acid halide corresponding to general formula II:

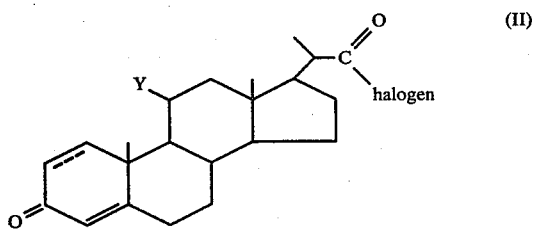
(II)

in which Y is as defined above, is reacted with a metal azide in an aqueous/organic two-phase reaction at a temperature of below about 25° C. the resulting carboxylic acid azide is hydrolyzed by heating in the pressure of an aqueous acid with elimination of nitrogen into the C20-amine, and recovering said Δ4-C21-steroid compounds.

17. A process as claimed in claim 16, characterized in that the reaction of the C20-carboxylic acid halide to form the corresponding azide is carried out using quaternary ammonium salts as phase transfer catalysts.

18. A process as claimed in claim 17 in which a reaction temperature of from 0° to 5° C. is utilized.

19. A process for the production of Δ4-C21-steroid compounds with a carbamate in the 20-position corresponding to general formula VII:

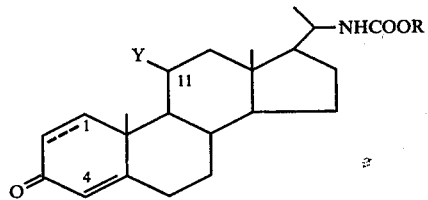

in which Y is a member selected from the group consisting of hydrogen, hydroxyl, and together with the C-atom substituted by Y, a carbonyl and a 9(11)-ene bond characterized in that a C20-carboxylic acid halide corresponding to general formula II:

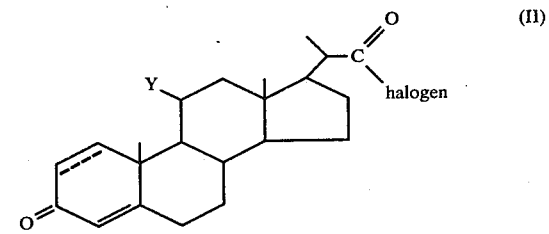

in which Y is as defined above, is reacted with a metal azide in an aqueous/organic two-phase reaction at a temperature of below about 25° C., the resulting carboxylic acid azide is recovered and heated to give the corresponding C20-isocyanate by the elimination of nitrogen and the C20-isocyanate thus obtained is converted into the C20-carbamate of general formula VII.

20. A process as claimed in claim 19 characterized in that the reaction of the C20-carboxylic acid halide to form the corresponding azide is carried out using quaternary ammonium salts as phase transfer catalysts.

21. A process as claimed in claim 20 in which a reaction temperature of from 0° to 5° C. is utilized.

* * * * *